United States Patent [19]
Mandal

[11] Patent Number: 6,165,426
[45] Date of Patent: Dec. 26, 2000

[54] METHOD OF PURIFYING LIQUID PRODUCTS BY REMOVING SOLUBLE ANTIMONY COMPOUNDS THEREFROM

[75] Inventor: Sanjay K. Mandal, Grand Island, N.Y.

[73] Assignee: Occidental Chemical Corporation, Dallas, Tex.

[21] Appl. No.: 09/356,198

[22] Filed: Jul. 16, 1999

[51] Int. Cl.⁷ .......................... C22B 30/00; C07C 17/00
[52] U.S. Cl. .............................................. 423/87; 570/167
[58] Field of Search ................................ 423/87; 570/167

[56] References Cited

U.S. PATENT DOCUMENTS

| | | | |
|---|---|---|---|
| 796,849 | 8/1905 | MacArthur | 423/87 |
| 3,806,589 | 4/1974 | Becher et al. | 423/87 |
| 3,872,210 | 3/1975 | Ukaji et al. | 423/87 |
| 3,883,345 | 5/1975 | Caldon et al. | 423/87 |
| 4,005,176 | 1/1977 | Fernschild et al. | 423/87 |
| 4,411,874 | 10/1983 | Lee | 423/87 |

FOREIGN PATENT DOCUMENTS 63-282126  11/1988  Japan ....................................... 423/87

OTHER PUBLICATIONS

Abstract, R. Ortwein et al., *Z. Anorg. Allg. Chem.* (1974), 408(1), pp. 42–52, "Water Adducts of Antimony(V) Chloride".

*Primary Examiner*—Steven Bos
*Attorney, Agent, or Firm*—Richard D. Fuerle; Anne E. Brookes

[57] ABSTRACT

Disclosed is a method of removing a soluble antimony compound from a liquid in which it is dissolved. The liquid is contacted with a hydrated compound, particularly a hydrated compound that forms carbonate ions, bicarbonate ions, or both in the liquid, such as carbonic acid or hydrates of sodium carbonate, sodium bicarbonate, potassium carbonate, potassium bicarbonate, ammonium carbonate, or ammonium bicarbonate. An antimony compound is formed that is insoluble in the liquid and it is separated from the liquid.

19 Claims, No Drawings

METHOD OF PURIFYING LIQUID PRODUCTS BY REMOVING SOLUBLE ANTIMONY COMPOUNDS THEREFROM

BACKGROUND OF THE INVENTION

This invention relates to a method of removing a soluble antimony compound from a liquid in which it is dissolved. In particular, it relates to the reaction of a hydrated compound, such as a hydrated carbonate or bicarbonate, with an antimony compound dissolved in a liquid to convert the soluble antimony compound into an antimony compound that is insoluble in the liquid.

Trifluoromethoxybenzene (TFMB) is an important commercial chemical intermediate used to make herbicides and other chemicals. It is typically made by reacting trichloromethoxybenzene (TCMB) with hydrogen fluoride, HF, at about 40 to about 45° C. in the presence of antimony pentachloride, $SbCl_5$, as a catalyst. The TFMB and the antimony pentachloride are miscible liquids and the antimony pentachloride dissolves in the TFMB. Some customers demand less than 5 ppm (parts per million, by weight) antimony in the TFMB product because antimony pentachloride is a Lewis acid and may catalyze side reactions in the next manufacturing step. Distilling the crude product in the presence of soluble antimony, however, may cause the decomposition of the product or further reactions of the product during distillation. Also, the presence of a metal, such as antimony, is not acceptable in chemicals used for electronic applications. Thus, to obtain an antimony-free product, it is necessary to either remove the soluble antimony catalyst prior to distillation or convert it to an insoluble form.

Antimony pentachloride can be removed from TFMB by heating it to a temperature of at least 140° C., which results in the precipitation of antimony trichloride. This approach, however, may result in the decomposition of some of the TFMB or its loss with the chlorine gas byproduct.

SUMMARY OF THE INVENTION

I have discovered that certain soluble antimony compounds, such as antimony pentachloride, can be removed from a liquid in which they are dissolved by reacting them with a hydrated compound, which results in the formation of an insoluble antimony compound. Using the process of this invention, it is possible to reduce the antimony content of TFMB from a typical range of 3000 to 30,000 ppm to less than 1 ppm. Color bodies (e.g., dimers and trimers) and residual acids (e.g., HCl and HF) are also removed using the process of this invention. The removal of HF also means that a glass still can be used to purify the product.

DESCRIPTION OF THE PREFERRED EMBODIMENTS

In the process of this invention, a soluble antimony compound is removed from a liquid in which it is dissolved. The liquid is typically the product of a reaction catalyzed by the antimony compound, but a solvent may also be present. The process of this invention is particularly useful when the antimony compound cannot be removed by filtration because it cannot be easily caused to precipitate (as, for example, by cooling), and it cannot be removed by distillation because it distills over with the product or the product cannot be distilled without degradation. Examples of antimony compounds that can be removed from solution using the process of this invention include antimony pentachloride, antimony pentafluoride, antimony dichlorotrifluoride, antimony trichlorodifluoride, and soluble adducts thereof. The process of this invention can be used to remove any amount of soluble antimony compound, but it is most practical if the amount of soluble antimony compound is between about 1 ppm and about 10 wt %.

Typically, the antimony compound is used to catalyze the liquid phase fluorination of a chlorine-substituted substrate and remains dissolved in the fluorinated product as an impurity. Examples of fluorination reactions that can be catalyzed with an antimony catalyst include TCMB to TFMB, benzotrichloride to benzotrifluoride, monochlorobenzotrichloride to mono-chlorobenzotrifluoride, 1,1,1-trichloroethane to 1,1,1-trifluoroethane, hexachloroxylene to hexafluoroxylene, and hexachloroxylene to trichlorotrifluoroxylene. Fluorinating agents useful in these reactions include hydrogen fluoride (HF), ammonium hydrogen fluoride (($NH_4$)$HF_2$), ammonium fluoride hydrogen fluoride ($NH_4F$•nHF) sodium hydrogen fluoride ($NaHF_2$), potassium fluoride (KF), trimethylamine hydrogen fluoride (($CH_3$)$_3$NHF), pyridinium hydrogen fluoride ($C_6H_5N$•HF), and antimony trifluoride ($SbF_3$), where n is 1 to 10. Hydrogen fluoride is the usual fluorinating agent as it is less expensive.

To remove the antimony compound from the liquid in which it is dissolved, the liquid is contacted with a hydrated compound that reacts with the soluble antimony compound to form an insoluble antimony compound, but does not react with the liquid itself. Examples of such compounds include carbon dioxide in water, which forms carbonic acid (dihydrogen carbonate), hydrated carbonates and bicarbonates such as sodium carbonate (soda ash), sodium bicarbonate, potassium carbonate, potassium bicarbonate, ammonium carbonate, ammonium bicarbonate, hydrated alumina, hydrated magnesium sulfate, and hydrated sodium sulfate. Hydrated compounds that form carbonate and/or bicarbonate ions in the liquid are preferred and carbonates are preferred to bicarbonates as they are about twice as effective. Sodium carbonate (soda ash) is preferred as it is inexpensive and has been found to work well. The compound must be hydrated, either when added or in situ, as anhydrous compounds do not work well. Pre-hydrated compounds are preferred as hydrating in situ may result in the presence of water in the product. One to ten waters of hydration can be present; sodium carbonates, for example, is sold as the monohydrate and as the decahydrate.

The hydrated compound can be mixed with the liquid, or the liquid can be passed through a column or bed of the hydrated compound, or a slurry of the hydrated compound can be passed through a column or bed of the hydrated compound. Alternatively, the hydrated compound can be contacted with the liquid followed by distillation as the precipitated antimony will remain in the pot. The use of a column is preferred for solid hydrated compounds as no filtration of the hydrated compound is required. A tall column is preferred for less breakthrough of the soluble antimony compound.

Sufficient hydrated compound should be used to remove all of the antimony. The amount used depends upon the degree of hydration of the hydrated compound; it also depends upon the amount of time that the hydrated compound is to be in contact with the liquid because most hydrated compounds only gradually release their water of hydration. For example, if a monohydrate is to be mixed with the liquid, about 3 to about 10 equivalents can be used, while only about 2 to about 4 equivalents of a decahydrate are needed. On the other hand, if the liquid is to be poured through a column of the hydrated compound, at least about 20 equivalents of the monohydrate may be needed and at least about 5 equivalents of the decahydrate may be needed due to the shorter contact time. For the same reason, if the hydrated compound is mixed with the liquid, more is required if the stirring time is short (e.g., about an hour) than if the stirring time is long (i.e., about 15 hours). If the hydrated compound is in a column or bed, a sufficient amount should be used to prevent breakthrough of the soluble antimony compound.

While I do not wish to be bound by any theories, I believe that the water of hydration reacts with the soluble antimony compound to precipitate the insoluble antimony compound. Nevertheless, the use of water alone, without the carbonate or bicarbonate, should not be used as it will result in acidic conditions that are highly corrosive. It may also react with the product to produce undesirable byproducts. Also, if water alone is used, the insoluble antimony compound collects between the organic phase and an aqueous phase, resulting in poor separation of the precipitated insoluble antimony compound from the product. When hydrated carbonate or bicarbonate is used, there is no aqueous phase and there is better separation of the insoluble antimony compound from the product. A hydrated compound, also, tends to release only so much water as is needed, thereby minimizing these problems.

The following examples further illustrate this invention. A 1 L stock of crude TFMB prepared by reacting TCMB with HF which contained 6400 ppm of soluble antimony was used in all examples.

EXAMPLES 1 to 13

20 g of the above stock solution was mixed with a carbonate, stirred, arid filtered and the filtrate was analyzed for antimony. The following table gives the conditions and the results:

| Example | Carbonate (g, equiv, wt %) | Stirring Time (hours) | Antimony (ppm) |
| --- | --- | --- | --- |
| 1* | $Na_2CO_3 \cdot 10H_2O$ 0.246, 2, 1.23 | 1 | 18 |
| 2 | $Na_2CO_3 \cdot 10H_2O$ 0.246, 2, 1.23 | 15 | 2.2 |
| 3* | $Na_2CO_3 \cdot 10H_2O$ 0.369, 3, 1.84 | 1 | 5.9 |
| 4 | $Na_2CO_3 \cdot 10H_2O$ 0.369, 3, 1.84 | 3 | 1.0 |
| 4a | $Na_2CO_3 \cdot 10H_2O$ 0.369, 3, 1.84 | 3 | 1.5 |
| 5 | $Na_2CO_3 \cdot 10H_2O$ 0.369, 3, 1.84 | 15 | 0.51 |
| 6 | $Na_2CO_3 \cdot 10H_2O$ 0.492, 4, 2.46 | 15 | 0.40 |
| 7* | $Na_2CO_3 \cdot H_2O$ 0.162, 3, 0.81 | 15 | 71 |
| 8 | $Na_2CO_3 \cdot H_2O$ 0.162, 3, 0.81 | 65 | 3.2 |
| 9 | $Na_2CO_3 \cdot H_2O$ 0.324, 6, 1.62 | 15 | 4.3 |
| 10 | $Na_2CO_3 \cdot H_2O$ 0.405, 7.5, 2.02 | 1 | 2.8 |
| 11 | $Na_2CO_3 \cdot H_2O$ 0.405, 7.5, 2.02 | 15 | 1.5 |
| 12** | $Na_2CO_3 \cdot H_2O$ 0.540, 10, 2.69 | 3 | 2.0 |
| 13* | $Na_2CO_3$ 0.138, 3, 0.69 | 15 | 2700 |

*Comparative
**$NaSb(OH)_6$ was found in the spent $Na_2CO_3 \cdot H_2O$

EXAMPLES 14 to 18

100 g of the stock solution was run through a column packed with a hydrated compound. About 95 g of the material was collected and analyzed for antimony. The following table gives the hydrated compound used, its amount, and the results:

| Example | Hydrated Compound | Amount of Hydrated Compound (g or wt %) | Antimony (ppm) |
| --- | --- | --- | --- |
| 14 | $Na_2CO_3 \cdot 10H_2O$ | 3 | 0.64 |
| 15 | " | 5 | <0.22 |
| 16 | $Na_2CO_3 \cdot H_2O$ | 6 | 0.95 |
| 17 | " | 8 | 0.68 |
| 18 | Hydrated Alumina | 3.5 | 0.40 |

EXAMPLE 19

150 g of the stock solution was mixed with 1.84 g of $Na_2CO_3 \cdot 10H_2O$ (2 equiv. or 1.23 wt %) and stirred for 1 hour. The mixture was filtered and the filtrate was run through a column packed with 3 g of $Na_2CO_3 \cdot 10H_2O$ (2 wt %). About 143 g of the material was collected and was found to contain 0.54 ppm of antimony.

I claim:

1. In a method of making a liquid product using an antimony catalyst wherein up to 10 wt % of said antimony catalyst dissolves in said liquid product, an improved method of separating said antimony catalyst from said liquid product comprising (A) contacting said liquid product with a hydrated compound selected from the group consisting of hydrates of sodium carbonate, sodium bicarbonate, potassium carbonate, potassium bicarbonate, ammonium carbonate, ammonium bicarbonate, and mixtures thereof, whereby said hydrated compound does not react with said liquid product but does react with said antimony catalyst to form an antimony compound that is insoluble in said liquid product; and (B) separating said insoluble antimony compound from said liquid product.

2. A method according to claim 1 wherein said antimony catalyst is antimony pentachloride.

3. A method according to claim 1 wherein said liquid product is trifluoromethoxybenzene.

4. A method according to claim 1 wherein said liquid product is poured through a column of said hydrated compound.

5. A method according to claim 4 wherein said liquid product is contacted with at least about 20 equivalents of said hydrated compound when said hydrated compound is a monohydrate and is contacted with at least about 5 equivalents of said hydrated compound when said hydrated compound is a decahydrate.

6. A method according to claim 1 wherein said hydrated compound is mixed with said liquid product.

7. A method according to claim 6 wherein said liquid product is contacted with about 3 to about 10 equivalents of said hydrated compound when said hydrated compound is a monohydrate and is contacted with about 2 to about 4 equivalents of said hydrated compound when said hydrated compound is a decahydrate.

8. A method according to claim 1 wherein said hydrated compound is sodium carbonate monohydrate or sodium carbonate decahydrate.

9. A method of removing about 1 ppm to about 10 wt % antimony pentachloride from trifluoromethoxybenzene comprising (A) contacting said trifluoromethoxybenzene with hydrated soda ash, whereby said antimony pentachloride reacts with said hydrated soda ash to form an insoluble solid antimony compound, and solid sodium chloride; and (B) separating said solid antimony compound and said solid sodium chloride from said trifluoromethoxybenzene.

10. A method according to claim 9 wherein said trifluoromethoxybenzene is poured over at least about 20 equivalents of said hydrated soda ash when said hydrated soda ash is a monohydrate and is poured over at least about 5 equivalents of said hydrated soda ash when said hydrated soda ash is a decahydrate.

11. A method according to claim 9 wherein about 3 to about 10 equivalents of said hydrated soda ash are mixed with said trifluoromethoxybenzene when said hydrated soda ash is a monohydrate and about 2 to about 4 equivalents of said hydrated soda ash are mixed with said trifluoromethoxybenzene when said hydrated soda ash is a decahydrate and the mixture is filtered and distilled.

12. A method according to claim 9 wherein the amount of antimony pentachloride in said trifluoromethoxybenzene is about 3,000 to about 30,000 ppm.

13. A method according to claim 9 wherein said trifluoromethoxybenzene was made by reacting trichloromethoxybenzene with hydrogen fluoride in the presence of said antimony pentachloride.

14. A method of making a fluorinated compound comprising (A) forming a solution of the corresponding chlorinated compound and an antimony catalyst;

(B) contacting said solution with a fluorinating agent, whereby said solution of said antimony catalyst in said chlorinated compound is converted into a solution of said antimony catalyst in said fluorinated compound;

(C) contacting said solution of said antimony catalyst in said fluorinated compound with a hydrated compound that forms carbonate ions, bicarbonate ions, or a mixture of carbonate ions and bicarbonate ions in said solution, whereby an insoluble antimony compound is formed; and (D) separating said insoluble antimony compound from said solution.

15. A method according to claim 14 wherein said chlorinated compound is trichloromethoxybenzene and said fluorinated compound is trifluoromethoxybenzene.

16. A method according to claim 14 wherein said antimony catalyst is antimony pentachloride.

17. A method according to claim 14 wherein said hydrated compound is selected from the group consisting of hydrates of sodium carbonate, sodium bicarbonate, potassium carbonate, potassium bicarbonate, ammonium carbonate, ammonium bicarbonate, carbonic acid, and mixtures thereof.

18. A method according to claim 17 wherein said hydrated compound is sodium carbonate monohydrate or sodium carbonate decahydrate.

19. A method according to claim 14 wherein the concentration of said antimony catalyst in said solution is about 1 ppm to about 10 wt %.

* * * * *